United States Patent [19]

Frankhouser

[11] Patent Number: 4,515,592
[45] Date of Patent: * May 7, 1985

[54] CATHETER SHIELD

[75] Inventor: Paul L. Frankhouser, Reading, Pa.

[73] Assignee: Arrow International, Inc., Reading, Pa.

[*] Notice: The portion of the term of this patent subsequent to May 4, 1999 has been disclaimed.

[21] Appl. No.: 374,480

[22] Filed: May 3, 1982

Related U.S. Application Data

[63] Continuation of Ser. No. 149,478, May 13, 1980, Pat. No. 4,327,723.

[51] Int. Cl.³ .............................................. A61M 25/00
[52] U.S. Cl. ...................................... 604/163; 604/171
[58] Field of Search .................... 604/53, 54, 158, 162, 604/163, 171, 172, 326, 243

[56] References Cited

U.S. PATENT DOCUMENTS

| 2,937,643 | 5/1960 | Elliot | 604/163 |
| 3,185,151 | 5/1965 | Czorny | 604/163 |
| 3,335,723 | 8/1967 | Waldman, Jr. | 604/163 |
| 3,709,223 | 1/1973 | Macalalad et al. | 604/163 X |
| 3,854,483 | 12/1974 | Powers | 604/172 |
| 3,898,993 | 8/1975 | Taniguchi | 604/172 |
| 4,029,099 | 6/1977 | Fifield | 604/326 |
| 4,062,363 | 12/1977 | Bonner, Jr. | 604/171 |
| 4,235,232 | 11/1980 | Spaven et al. | 604/171 X |
| 4,327,723 | 5/1982 | Frankhouser | 604/171 |

Primary Examiner—Robert P. Swiatek
Attorney, Agent, or Firm—Charles H. Lindrooth

[57] ABSTRACT

Disclosed is a shield assembly for a catheter particularly useful for the protection of flow directed catheters used in the measurement of central venous pressure and pulmonary wedge pressure. The shield assembly includes front and rear hubs each with a central passage sized to permit movement of a catheter therethrough and a feed tube for interconnecting the front and rear hubs. The feed tube has a lumen extending between the passage and the hubs for guiding a catheter passed through the rear hub and out through the front hub. A flexible sheath interconnects the two hubs. The sheath is substantially longer than the feed tube and is collapsible to permit interconnection of the two hubs by the feed tube for catheter guidance during feeding of the catheter through the rear hub, through the feed tube and through the front hub and is extendable to shield a substantial length of catheter from contamination when the front and rear hubs are separated.

8 Claims, 6 Drawing Figures

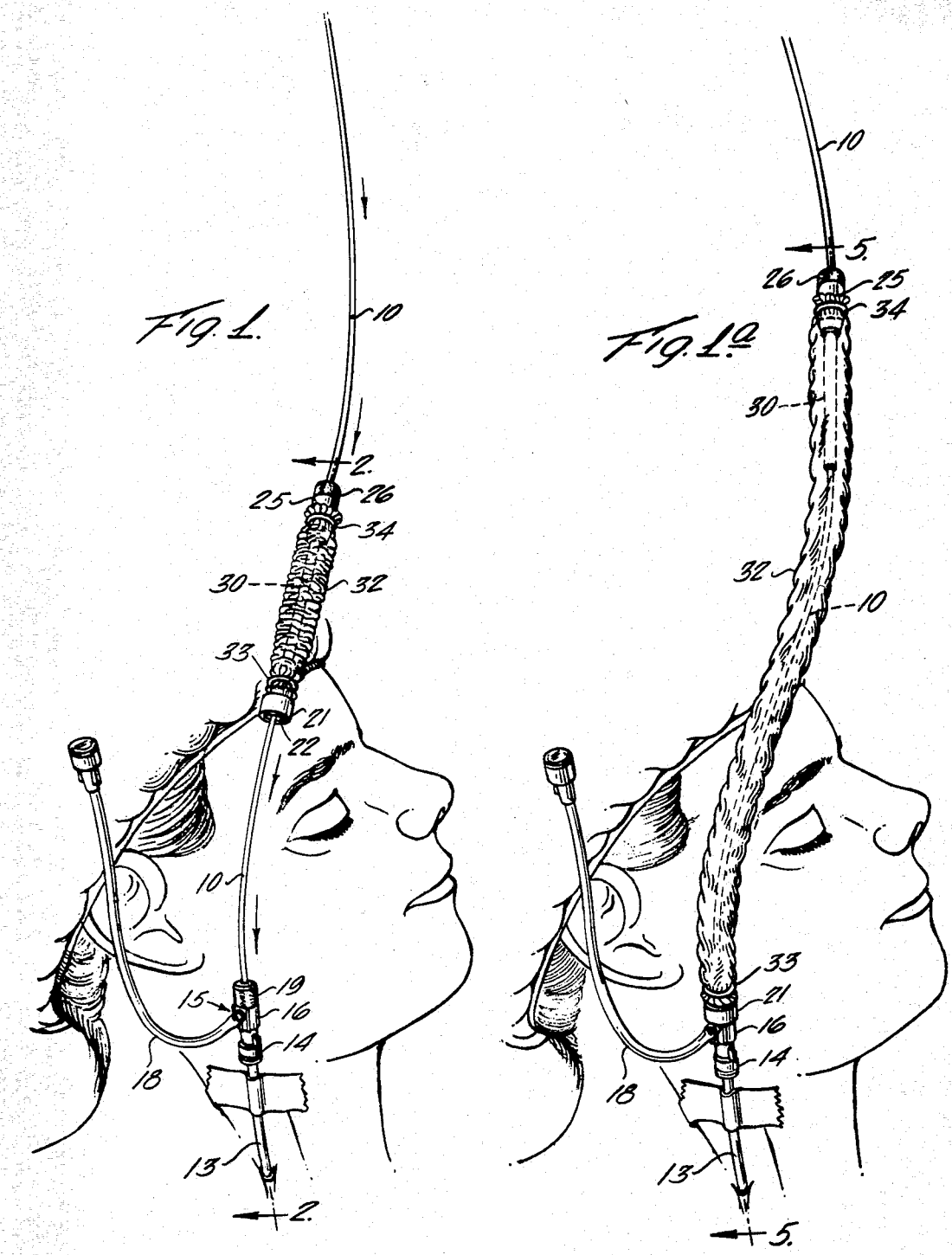

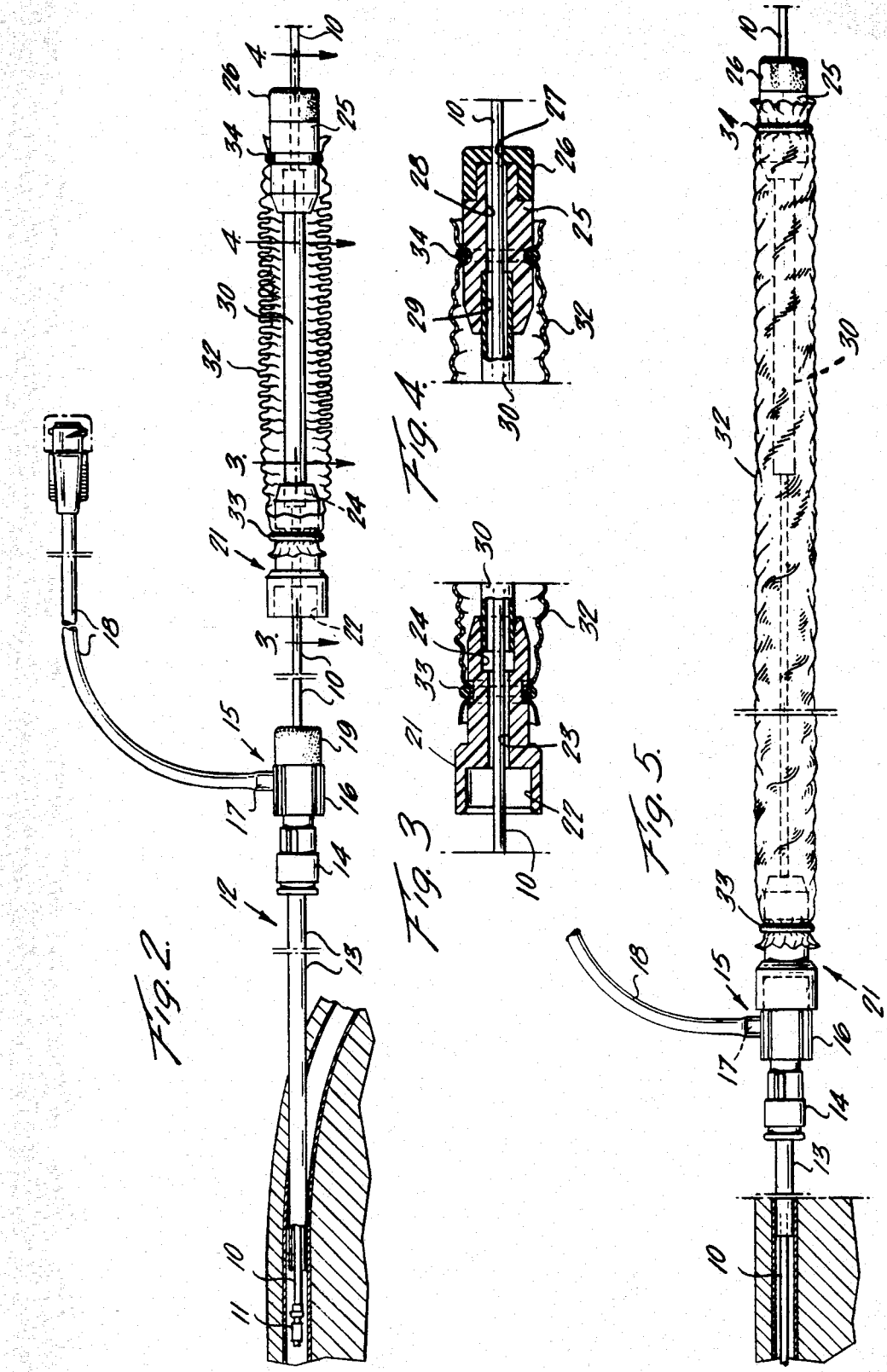

CATHETER SHIELD

This application is a continuation of application Ser. No. 149,478, filed May 13, 1980, now U.S. Pat. No. 4,327,723.

FIELD OF THE INVENTION

This invention relates to apparatus for protecting a catheter from contamination during and after the time the catheter is inserted into a venous lumen or other body cavity of a human or animal.

BACKGROUND AND THE PRIOR ART

The invention is particularly useful for the protection of flow directed catheters used in the measurement of central venous pressure and pulmonary wedge pressure during and after cardio-pulmonary bypass surgical procedures.

In these procedures, the patient is monitored using a pulmonary artery balloon tipped catheter having at least two lumens. The catheter is placed percutaneously before induction of anesthesia. In certain instances it has been observed that the balloon of the catheter will fail to wedge after cardio-pulmonary bypass and the catheter has to be repositioned. Manipulation of the catheter to reposition it is recognized to be hazardous because over a period of time exposed segments of the catheter may have become contaminated and introduction of this exposed portion may cause infection.

In accordance with prior art practice for the insertion of the catheter, a vein such as the right internal jugular vein of the patient is entered with a hollow needle over which a teflon radio-opaque catheter may be placed. If the radio-opaque catheter is used the needle is removed and a stainless steel wire guide is then introduced through the catheter into the lumen of the vein. After removal of the catheter, an introducer device is passed over the guide through a small incision into the lumen of the vein. The wire guide is then removed and the flow directed catheter inserted and positioned through the introducer device. Known practice also involves the use of a plastic sheath which is tied or otherwise secured at one end to the introducer. After the catheter has been completely advanced to the wedge position, the opposite end of the sheath is fully extended over the catheter to a position remote from the introducer. This end is then fastened in place by a sterile fastening so that a length of catheter between the introducer and the opposite end of the sheath is maintained in sterile condition. This length, which may be as long as 25 in., can be advanced easily into the vein if the catheter again has to be moved to the wedge position after dislodgement or migration.

The present invention relates to improvements in method and apparatus of catheter placement and protection by providing a disconnectible guide tube means within a flexible sheath for ease of feeding a catheter through the assembly comprising the plastic sheath extending between front and rear hubs particularly when used with an adapter with side port and catheter introducer.

OBJECTS AND ADVANTAGES OF THE INVENTION

An important object of the invention is the provision for the protection from contamination of a length of an indwelling catheter thereby providing a reserve catheter portion which can be advanced into the body should the catheter require repositioning.

A further objective of the invention is the provision of simplified means providing for a sterile section of a catheter within a protective sheath which can easily and safely be advanced into the patient's body after dislodgement or migration of the catheter without fear of contamination of the patient.

A still further object of the invention is the provision of a catheter sterility shield which incorporates novel guide tube means for ease of advancement of the catheter through the protective shield when the catheter is prepared for insertion into the patient's body.

The foregoing and various other objectives which will become apparent from the following detailed description, are achieved by an assembly for an indwelling catheter comprising a rigid flanged front hub, a rear hub and an interconnecting elongated collapsible flexible sheath of transparent plastic material which is secured and sealed to the periphery of the front and rear hubs. Interconnecting the two hubs is a feed tube means preferably comprising a clear feed tube secured to one of the hubs and frictionally interconnected with the other hub. When interconnected, the length of the assembly is substantially shorter than the length of the flexible transparent plastic sheath. The rear hub is provided with an opening for advancement of a catheter through the feed tube means and through the front hub for subsequent feeding into an introducer for insertion into the patient's body. Sealing means are provided at the front and rear hubs to prevent the migration of microbiological contaminants into the shield portion of the sheath. Preferably just prior to insertion to the patient's body, while all parts are still in a sterile condition, the sheath is extended so as to provide a reserve length of catheter which is always maintained in a sterile condition.

BRIEF DESCRIPTION OF THE DRAWINGS

In the detailed description which follows, reference is made to the following figures of the drawings, illustrating a preferred embodiment of the invention:

FIG. 1 shows in diagrammatic form a catheter shield assembly with the catheter in the process of being advanced through the internal jugular vein of a human patient;

FIG. 1a is a schematic view showing the catheter after placement, with the catheter shield in the fully extended position;

FIG. 2 is a plan view, partially in section, illustrating a catheter shield assembly with parts in position corresponding to FIG. 1;

FIG. 3 is a sectional view taken along line 3—3 of FIG. 2;

FIG. 4 is a sectional view taken along line 4—4 of FIG. 2; and

FIG. 5 is a plan view, partially in section, of the catheter shield assembly with parts in position corresponding to that which is illustrated in FIG. 1a.

DETAILED DESCRIPTION OF THE DRAWINGS

Referring now to the drawings and in particular FIGS. 1 and 2, there is shown a catheter 10, which is typically of the flow directed type. As known in the art, these catheters are provided with a plurality of lumens, not shown, one of which is in communication with an inflatable balloon 11 located immediately adjacent the catheter tip. Briefly, the balloon is inflated after the catheter is placed intra thoracic and the balloon acts to gently carry the catheter through the blood stream and through the chambers of the heart into the narrowing of the pulmonary artery where it is wedged in place. The catheter is designed to monitor cardiac output in the pulmonary artery through a second lumen. Multilumen flow directed catheters capable of giving other indications of heart function have come into widespread use and give the attending physician an immediate diagnosis or indication of a patient's cardiac problems.

In accordance with preferred technique, as described above, a hollow introducer 12 comprised of an elongated tubular portion 13 and an enlarged end portion 14 having a Luer lock-type female fitting is inserted into the selected vein and taped in place.

A side port adapter assembly 15 of known construction is provided with a body portion 16 which includes a male Luer lock-type coupling for connection with the female part of the introducer 12. A side port 17 onto which is fitted a section of tubing 18 is provided for purposes to be described subsequently. Preferably, the rear end of body portion 16 is provided with a sealing member 19 having an opening extending therethrough for passage of the catheter 10 into the hollow introducer. Sealing member 19 is preferably formed of soft rubber so that the opening has good sealing characteristics with the catheter 10. The outer periphery frictionally interfits with the front hub of the catheter shield assembly about to be described.

The catheter shield assembly includes a front hub made of a rigid sterilizable plastic material as best shown at 21 in FIG. 3, the front hub includes a flanged portion 22 which receives and sealingly interfits with the rubber hub 19. An internal passageway slightly larger in diameter than the catheter extends through the hub. The rear portion of the hub is provided with a socket 24 for purposes to be described hereinafter.

FIG. 4 illustrates the rear hub of the assembly. The rear hub comprises a body 25 on the rear end of which is fitted a sealing part 26 having opening 27 through which the catheter is passed. Part 26 is preferably formed of soft rubber or other yieldable material having good sealing characterics and yet capable of passing the balloon tip of the catheter without damage to that fragile portion. The body of rear hub 25 has an axial passage 28 extending therethrough of slightly enlarged diameter as compared with the opening in the soft rubber sealing part 26. A socket 29 is provided in the front end of the rear hub and receives a length of clear, relatively rigid tubing 30. In the preferred embodiment, the end of the tubing 30 is press fit or otherwise secured within the socket 29. The other end of tubing 30, as best illustrated in FIG. 3 is frictionally fit within the socket portion 24. The fit is such that a slight pulling pressure on the two hubs readily separates the tubing from socket 24. Tubing 30 is preferably made of a transparent plastic material such as polyvinyl chloride and provides a guide tube means for a catheter as will be described hereinafter.

Interconnecting the two hubs is a transparent sheath 32 formed of a transparent flexible material such as polyethylene or other plastic capable of preventing the passage of contaminants to the interior of the sheath. The sheath is secured and sealed to the front and rear hubs by means such as O-rings 33 and 34 although other means of sealing including ultrasonic bonding may be employed. Sheath 32 is substantially longer than the distance between the two hubs and bunches up or collapses when the inner feed tube 30 is fitted within the socket 24.

In use, the elements of the assembly described above together with the catheter and other instruments and equipment necessary for preparing the patient and positioning the introducer are supplied to the physician in sterile condition. The catheter is preassembled with the shield assembly, with the parts of the shield assembly illustrated as in FIG. 2 by advancing the catheter through the rear hub, through the guide tube means and the front hub. The catheter is advanced until the desired length indicator mark such as the 50 cm mark which is visible on its periphery, is passed out through the front hub. Where the side port assembly is used, the end of the catheter is passed through the passageway in the body of the side port assembly and advanced until about one inch extends beyond the end of the sideport assembly. The catheter can then be tested for balloon integrity. The Luer lock fittings of the introducer and the side port assembly are then interfitted and the catheter is then slowly advanced through the introducer. As soon as the tip of the catheter is intrathoracic, the balloon is inflated and the catheter is gently advanced to the wedge position. At this point there should be about 5 inches of exposed catheter between the side port assembly and the front hub. The front hub 21 is then pulled forward so that the guide tube disconnects from the front hub. The flanged socket 22 of hub 21 is advanced and fitted over sealing part 19. The protective sheath 32 then extends over the reserve length of catheter which is to be protected from contamination. Contamination is thus prevented from the introducer back to the opening 27 in the soft rubber sealing member 26. Should it become necessary to reposition the catheter, the reserve length within the protective sheath 32 is available for advancement into the patient's body without risk of contamination. The transparency of the sheath permits ready viewing of the length markings on the catheter so that the length of catheter within the patient can be readily determined. Side port 18 permits the introduction of a heparin solution through the introducer into the venous lumen and may be used for blood samplings as will be understood by those skilled in the art.

Although the invention is described for use with flow directed catheters used for the measurement of pulmonary artery wedge pressure, it should be understood that it is of use for a variety of applications wherein an indwelling catheter or catheter type device is introduced into the body wherein repositioning may be required from time to time.

I claim:

1. An assembly for the insertion and protection of a length of an indwelling catheter from sources of contamination external of the body of the patient, said assembly comprising in combination, a catheter introducer comprised of an elongated tube adapted to be inserted into a patient's blood vessel for introduction of a catheter into said vessel, a disconnectible fitting having a lumen therethrough and adapted to be connected to said introducer, said disconnectible fitting providing a seal for the lumen and the interior of the introducer against contamination from sources external of the body of the patient, a socket at the rear end of said lumen, a catheter guide tube frictionally interfitting within said socket and extending rearwardly therefrom, a hub connected to the rear end of said guide tube, a lumen in said hub providing for free passage of a catheter through the hub, through said guide tube through said disconnectible fitting and further through the catheter introducer, a flexible sheath covering said guide tube and sealingly interconnected to said disconnectible fitting and said hub, said sheath being collapsible to permit interconnection of the said rear hub and said disconnectible fitting by means of said catheter guide tube, for advancement of a catheter first through the rear hub, then through the guide tube and the disconnectible fitting until a length of a catheter needed for introduction into the patient is advanced beyond the end of said disconnectible fitting, the sheath being extendible to shield a substantial length of catheter beyond that advanced for introduction into the patient, the assembly comprising the introducer, the disconnectible fitting, the extended sheath and the hub all providing for isolation of the length of catheter advanced beyond the opening in the rear hub.

2. A method of catheterization which provides protection for a segment of the catheter against contamination, said method comprising providing a protective shield assembly for the catheter, said shield assembly having front and rear hub members, and guide tube means having a lumen, the guide tube means releasably interconnecting said front and rear hub members so as to provide a disconnectible assembly including the rear hub member, the front hub member and the guide tube means, an elongated transparent plastic sheath covering said guide tube means and sealingly interconnecting said front and rear hub members, said transparent sheath being substantially longer than said guide tube means, and being collapsible when the guide tube means interconnects the front and rear hub members, said front and rear hub members having openings coaxially aligned with said guide tube means when the guide tube means interconnects the lumen of the hub members, the guide tube means and said openings being adapted to receive and pass a catheter through the rear hub member, through the guide tube means and out through the front hub member when the guide tube means interconnects the hub members, the steps which comprise first passing the catheter through the rear hub member, the lumen of the guide tube means, the front hub member and then disconnecting the front and rear hub members and extending the sheath over a substantial length of the catheter by relative displacement of the front and rear hub members along the catheter thereby providing isolation of a substantial length of catheter from contaminants.

3. A shield assembly for an indwelling catheter advanced into the body through a tubular introducer, said assembly comprising, a front hub member, means interconnecting the front hub member with the introducer, feed tube means extending rearwardly from the front hub member, a passageway through the front hub member providing for the passage of a catheter advanced through the feed tube means, the front hub member and the introducer, a sheath formed of a flexible material secured to said hub member and extending over the feed tube means, said sheath being substantially longer than the feed tube means, rear sealing means at the end of said sheath opposite to the hub member for sealing the sheath to the catheter, the sheath being collapsible to facilitate passage of the catheter through the feed tube means and thereafter being extendible to shield a substantial length of catheter between the hub member and the rear sealing means, said rear sealing means comprising a rear hub member having an opening surrounded by a resilient material through which the catheter passes, said feed tube means being secured to the rear hub member with its passage in coaxial alignment with the opening in the rear hub member, the opposite end of said feed tube means being frictionally interfit with the front hub member and being separatable therefrom to permit extension of the sheath.

4. A shield assembly according to claim 3 wherein the sheath and the feed tube means are formed of transparent plastic materials.

5. A method of catheterization which provides protection for one portion of the catheter not within a patient against contamination while an adjacent portion is within the patient, said method comprising providing a protective shield assembly for the catheter, said shield assembly having a front hub, a rear sealing means and tube means extending between said front hub and rear sealing means, an elongated transparent plastic sheath covering said tube means and sealingly interconnecting said front hub and rear sealing means, said transparent sheath being extendible and when extended being substantially longer than said tube means and being collapsible when the front end of the tube means is adjoining the front hub, said front hub and rear sealing means being adapted to receive and pass the catheter through the rear sealing means, through the tube means and out through the front hub when the end of the tube means is adjoining the front hub the method further comprising first passing the catheter through the rear sealing means, then through the lumen of the tube means the front hub, and then separating the front hub and rear sealing means and extending the sheath over a substantial length of the catheter, thereby providing isolation of a substantial length of catheter from contaminants.

6. An assembly for the shielding of an elongated section of a percutaneously introduced indwelling balloon tipped catheter wherein successive portions of the elongated section are introduced into a blood vessel upon advancement of the catheter through the vessel, said assembly comprising a hub member having a passageway extending axially therethrough, a catheter introducer extending from the hub member, the introducer having an axially extending lumen in communication with the passageway through the hub member, a sheath formed of a flexible material fixed to and extending from the hub member in the direction opposite to the direction of extension of the introducer, the sheath being in sealing relationship with the hub member, a catheter guide tube within said sheath, means for securing the opposite end of said sheath in sealing relationship with said catheter guide tube, said sheath being substantially longer than said guide tube and being collapsible to a position in which the front end of the guide tube is adjoining the hub member with the lumen of the guide tube in registry with the passageway through the hub member to facilitate feeding of a catheter through the guide tube and said passageway, said collapsible sheath being extendible to shield a substantial length of catheter and disconnectible means comprising a socket in said hub member coaxial with the passageway therethrough, said socket being within said sheath and being dimensioned to receive the free end of said guide tube with a friction fit between the said free end and the socket to permit separation of the said free end from the socket and extension of the sheath over an elongated section of catheter.

7. An assembly according to claim 6 wherein said sheath is formed of a transparent plastic material.

8. An assembly according to claim 7 wherein said guide tube comprises a length of transparent plastic tubing.

* * * * *

UNITED STATES PATENT AND TRADEMARK OFFICE
CERTIFICATE OF CORRECTION

PATENT NO.   : 4,515,592
DATED        : May 7, 1985
INVENTOR(S)  : Paul L. Frankhouser It is certified that error appears in the above-identified patent and that said Letters Patent is hereby corrected as shown below:

| | |
|---|---|
| Col. 3, line 31 | "material as" should read --material. As-- |
| Col. 3, line 43 | "characterics" should read --characteristics-- |
| Col. 6, line 26 | "hub the" should read --hub, the-- |
| Col. 6, line 28 | "tube means the" should read --tube means and the-- |

Signed and Sealed this

Twenty-sixth Day of November 1985

[SEAL]

Attest:

DONALD J. QUIGG

*Attesting Officer*   *Commissioner of Patents and Trademarks*